(12) United States Patent  (10) Patent No.: US 7,467,869 B2
Kahlen  (45) Date of Patent: Dec. 23, 2008

(54) SYSTEM AND METHOD FOR ACQUIRING DATA AND ALIGNING AND TRACKING OF AN EYE

(75) Inventor: Bjorn Kahlen, Bremen (DE)

(73) Assignee: Bausch & Lomb Incorporated, Rochester, NY (US)

( * ) Notice: Subject to any disclaimer, the term of this patent is extended or adjusted under 35 U.S.C. 154(b) by 106 days.

(21) Appl. No.: 10/550,437

(22) PCT Filed: Mar. 31, 2004

(86) PCT No.: PCT/EP2004/003415

§ 371 (c)(1), (2), (4) Date: Aug. 16, 2006

(87) PCT Pub. No.: WO2004/089214

PCT Pub. Date: Oct. 21, 2004

(65) Prior Publication Data

US 2007/0091264 A1  Apr. 26, 2007

(51) Int. Cl.
*A61B 3/14* (2006.01)
(52) U.S. Cl. ........................ 351/206; 351/205
(58) Field of Classification Search ............. 351/205, 351/206; 382/117
See application file for complete search history.

(56) References Cited

U.S. PATENT DOCUMENTS 5,291,560 A   3/1994   Daugman

2002/0097378 A1   7/2002   Saito et al.

FOREIGN PATENT DOCUMENTS

| WO | WO 01/28476 A | 4/2001 |
|---|---|---|
| WO | WO 01/78584 | 10/2001 |
| WO | WO 01/89373 A | 11/2001 |
| WO | WO 02/064031 | 8/2002 |
| WO | WO 02/087442 A | 11/2002 |

OTHER PUBLICATIONS

Williams, "Iris Recognition Technology," IEEE Aerospace and Electronic Systems Magazine, IEEE Inc. (New York, NY), vol. 12 (No. 4), p. 23-29, (Apr. 1, 1997).
Wildes, "Iris Recognition: An Emerging Biometric Technology," Proceedings of the IEEE, IEEE Inc. (New York, NY), vol. 85 (No. 9), p. 1348-1363, (Sep. 1, 1997).

*Primary Examiner*—William C Choi

(57) ABSTRACT

A system and a corresponding method is provided for aligning and/or tracking of an eye of a patient with reference to an ophthalmic unit for performing diagnosis and/or treatment of the eye. The system comprises means for providing a previously acquired iris code of the eye, an iris recognition unit for acquiring an iris code of the eye under investigation and a comparator for comparing the previously acquired iris code with the present iris code and to provide a comparison result. The ophthalmic unit performs said diagnosis and/or treatment of the eye when said comparison result is greater than an identification determining level.

37 Claims, 2 Drawing Sheets

SYSTEM AND METHOD FOR ACQUIRING DATA AND ALIGNING AND TRACKING OF AN EYE

Figure 1:
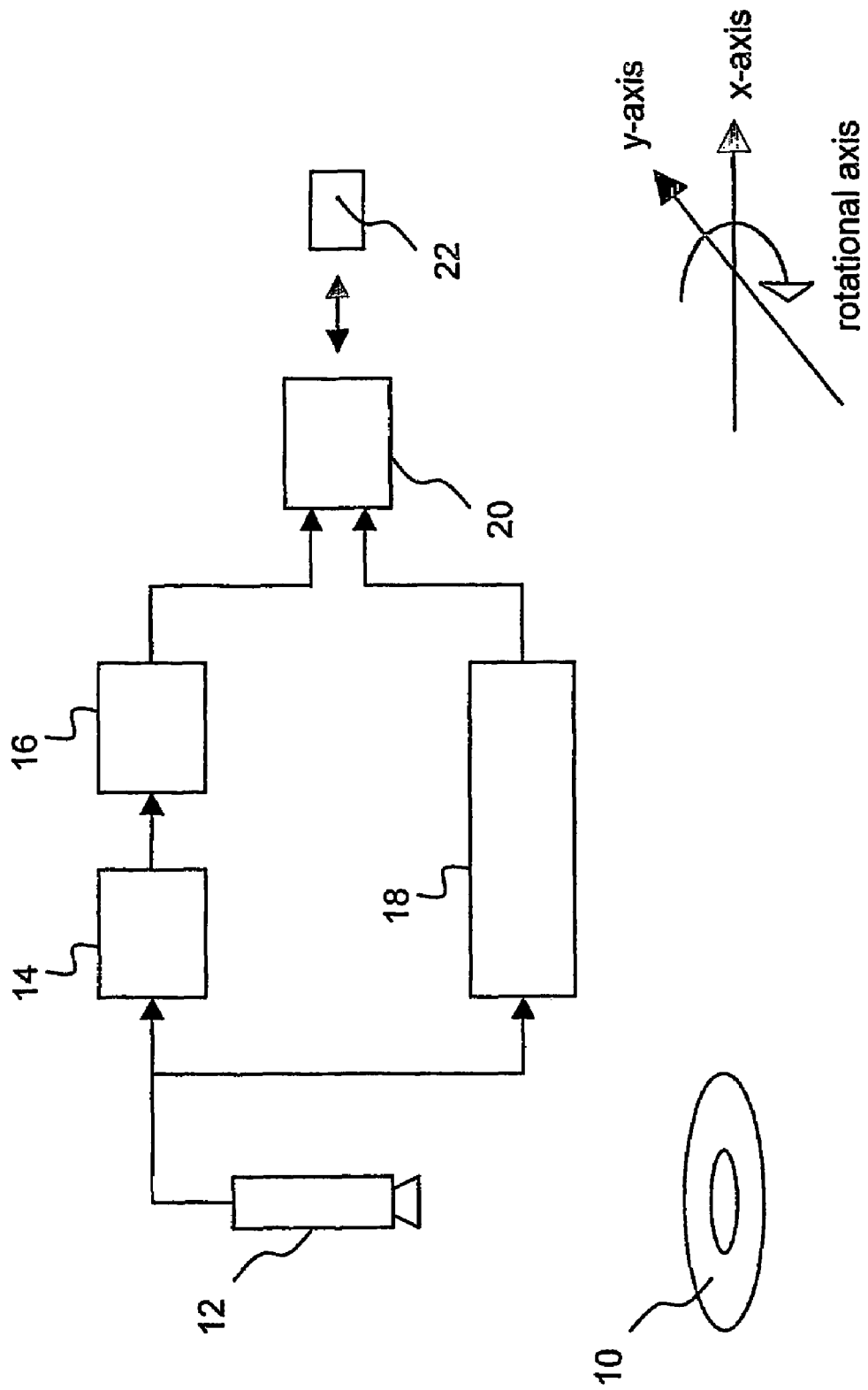

The invention is generally directed to the field of diagnosis and treatment of an eye and is more particularly directed to a system and method for acquiring data of an eye of a patient and a system and method for aligning and tracking an eye during diagnosis and treatment.

WO 01/78584 A2 discloses eye registration and a stigmatism alignment control systems and a corresponding method. An orientation system for corrective eye surgery includes a camera for performing a first image mapping a patient's eye using a predetermined eye feature and software for processing the first image map to determine an edge location of the feature. A second image mapping is performed with the patient in a different position. The second image map is processed to locate the feature. Alternatively, a pen is used to make two alignment marks on the eye. The eye is imaged with a patient in another position, and the image displayed. Software superimposes a graphical reticle onto the eye image, which is movable to align with the two alignment marks. In both cases software also calculates an orientational change to be applied to a corrective prescription for a surgical procedure to be performed on the eye with a patient in the second position.

In US 2002/0097378 A1 an apparatus and a method for pupil measurement and a refraction correction apparatus is described. The pupil measurement apparatus comprises a video camera for obtaining an image of an eye ball. It further comprises a processing unit for calculating a position and torsion of a pupil of the eye ball and an indicating unit for outputting the calculated position and torsion angle. The result may be used for automated adjustment during refractive laser surgery. More specifically, a central position arithmetic device determines the central position of the pupil which is compared with the reference position of the pupil. Furthermore, a torsion angle arithmetic device receives image data which has undergone filtering and polar coordinates/orthogonal transformation. In this unit the received image data are correlated with previously stored image data of the eye. By rotating the stored image data about a rotational axis through a predetermined rotation angle a correlation value is calculated for each of a plurality of rotation angles using a mutual correlation function. The value of a rotation angle at which the correlation value is maximized is calculated as a tortion angle.

WO 02/064031 A2 relates to multidimensional eye tracking and a position measurement system for diagnosis and treatment of the eye. More specifically, an image obtained from an imaging device is processed to measure horizontal, vertical and torsional positions of the eye by determining the position of natural or artificial landmarks on the eye such as among others pupil, iris structures, iris/limbus border, blood vessels, applied markers/marks, reflections of the illumination, the LASIK flap borders of the cornea and also laser applied markings on the cornea. Pupil size independent tracking is obtained by periodically correcting any offsets of pupil center introduced by pupil dilation or other factors. The correction is realised by means of parallel tracking of reference points which are known to be stable with respect to the cornea during surgery, such as, for example, limbus border. A torsional eye tracking is performed by means of registration of at least two distinct landmarks on the eye. In an initialisation step a reference image is acquired and analysed in order to determine the suitable landmarks for registration and such reference points are stored as image templates together with their position relative to pupil center. In a tracking step the template of each reference point is searched in the incoming image by means of cross-correlation techniques. The torsion between the reference and current image is computed by optimal least-squared approximation of rotation matrix of the reference template and correspondent template.

The object underlying the present invention is to provide a system and method for acquiring data of an eye and a system for aligning and tracking of an eye with reference to an ophthalmic unit for performing diagnosis or treatment of the eye which does not need marking of the cornea and which is more accurate and faster and provides additional safety features.

This object is solved with the features of the claims.

According to a first aspect of the invention a system and the corresponding method is provided for acquiring data of an eye of a patient comprising a diagnosis unit for acquiring diagnosis data of the eye and an iris recognition unit for acquiring an iris code of the eye.

According to a further aspect of the invention a system and a corresponding method is provided for aligning and/or tracking of an eye of a patient with reference to an ophthalmic unit for performing diagnosis and/or treatment of the eye wherein said system comprises means for providing a previously acquired iris code of the eye, an iris recognition unit for acquiring an iris code of the eye under investigation and a comparator for comparing the previously acquired iris code with the present iris code and to provide a comparison result, wherein said ophthalmic unit performs said diagnosis and/or treatment of the eye when said comparison result is greater than an identification determining level.

An iris recognition unit which is especially suitable for use in the system and the method according to the first and the second aspect of the invention comprises an image pick-up unit for acquiring an image of the eye, an image processing unit for determining iris information at a plurality of positions of the image of the eye and a generating unit for generating an iris code based on the determination of the iris information at the plurality of positions of the image of the eye.

Basically, the present invention has the ability to perform iris recognition of human eyes which is used in two ways for diagnosis or treatment of an eye in particular for refractive laser treatments. Specifically in refractive laser treatments the present invention provides first a "fingerprint" of the iris which is used to track cyctorsions and pupil center shift in the patients eyes for the alignment of the laser ablation pattern. The invention is specifically suitable for compensating an eye rotation occurring between diagnostic measurements with a diagnosis unit such as a Zywave aberrometer where the patient is sitting up right and the laser treatment performed when the patient is lying horizontally. The invention further compensates for pupil center shift between diagnostic measurements at the Zywave aberrometer when the pupil is dilated and the laser treatment when the pupil is not dilated. Both positioning parameters are rated to have a significant impact on the clinical outcomes of customised treatments. The present invention further provides added safety features as the iris recognition feature is added to any diagnosis data so that in particular the potential for the wrong diagnostic being used to treat the patient for example the left eye versus right eye is eliminated.

Moreover, the invention provides an accurate, fast and reliable alignment and/or tracking of the eye by using an eye tracker camera operating at the sampling rate which is increased from the current 120 Hz to 240 Hz or 360 Hz so that the overall reaction time of the whole compensation system is significantly improved.

According to a preferred embodiment of the invention the alignment/tracking of the eye is performed in all possible dimensions in particular along an X and Y-axis, rotational direction and with respect to the Z-axis, i. e. in the height direction.

The technology of the present invention in particular the iris recognition feature could be used in the complete ophthalmologic field to store the iris information specific for every individual patient onto a "Patient Diagnostic Chip Card". Whenever the patient is examined or treated with an ophthalmologic instrument the iris code could be used to identify the person and upload or store all patient related information by analysing the iris structure with an iris recognition unit according to the present invention at the system.

The present invention provides the following advantages over the prior art. No marking of the cornea is necessary. Due to computed iris analysis more accurate recognition of the cyclotortion is available. The invention allows for faster surgical routine. The invention adds additional safety due to iris recognition.

Figure 2:
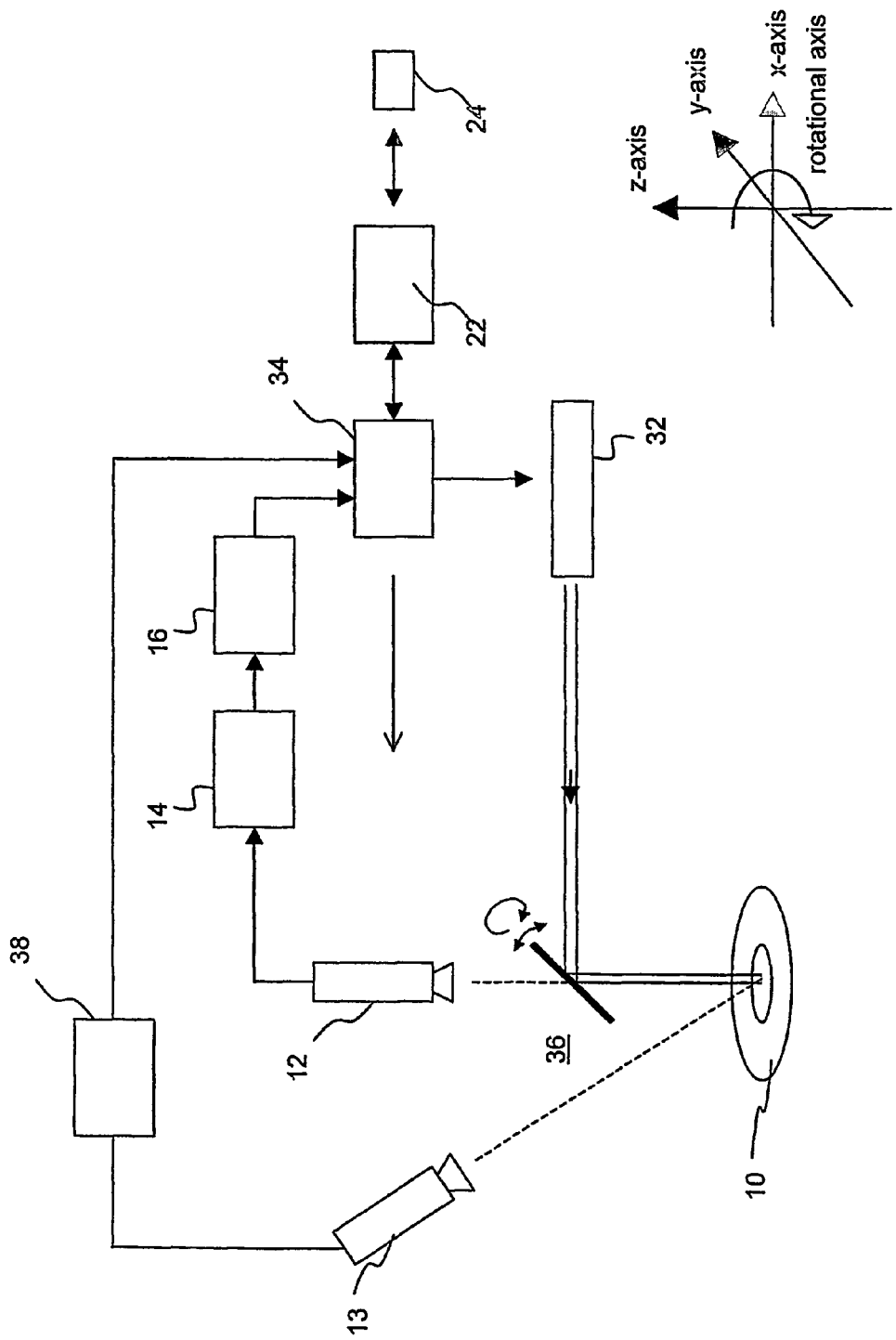

The present invention will be described in further detail by way of reference to preferred examples and the drawings in which FIG. 1 is a schematic illustration of a first preferred embodiment of the present invention, and FIG. 2 is a schematic illustration of a second preferred embodiment of the present invention.

A preferred embodiment of a system for acquiring data of an eye of a patient is shown in FIG. 1. As shown in the schematic illustration this system basically comprises a camera as an image pick-up unit 12 for acquiring images of an eye 10. These images are processed in an image processing unit 14 for determining the structure of the iris at a plurality of positions of an image of the eye. A generating unit 16 receives the processed data from the image processing unit 14 and generates an iris code which is provided to an input/output device 20. The system further comprises a diagnosis unit 18 which receives images from the image pick-up unit 12. As a diagnosis unit the Zywave aberrometer may be used for diagnostic measurement of the eye. In this preferred embodiment the input/output device is provided for reading and writing a chip card 22 of a patient.

In the following the functioning of this system is described with reference to one specific example. For performing the diagnostic measurement a Zywave aberrometer is used. At the beginning, for example, five images are taken of the undilated eye of the patient sitting up right in front of the camera 12. For the diagnosis measurement three out of five images may be taken for calculating an average wavefront. For the iris recognition one out of these five pictures may be selected according to one or two of the following criteria. There was no movement of the eye when taking the image and/or the image with the greatest size of the open eye is selected. It is possible to use a video camera preferably working in the infrared region as an image pick-up unit which acquires successively images or two half pictures for each image. By comparing the successive images or the two half pictures of each image a decision may be made whether there was any movement of the eye. Furthermore, the image may be selected according to a comparison of the area of the iris present in an image. It is preferred that the eye to be diagnosed is as wide as possible in order to recognize the edge of limbus and in order to recognize the whole or at least a large proportion of the iris. According to a preferred embodiment at least 50% of the iris should be present in an image.

According to the present embodiment the image processing unit determines the structure of the iris at a plurality of positions preferably at about 1,000 to about 10,000 positions of the iris, more preferably at about 2,000 to 6,000 positions of the iris and in a preferred embodiment at about 4,000 positions of the iris. At each of these positions at least two pixels, preferably at least two groups of pixels are compared. Specifically, the grey values of the pixels in this example may lie between 0 and 127. The grey value of each pixel or the respective average of grey values of a group of pixels is compared. If, for example, two neighbouring pixels or two neighbouring groups of pixels are compared with respect to their grey values the grey value of the pixel on the left hand side may be higher than the grey value of the pixel on the right hand side at a specific position. The result of this comparison may be given as a binary value "0". On the other hand, if the grey value of a pixel on the right hand side is darker than the grey value of the pixel on the left hand side with reference to a particular position than the comparison result would be "1". In the preferred embodiment the following comparisons are made at one selected position of the iris. At any position, the pixels present in an inner ring around a selected position, the pixels present in a middle ring surrounding the inner ring and the pixels in an outer ring surrounding the middle ring are investigated for this comparison. Furthermore, the pixels above and below the X-axis and the pixels at left hand side and the right hand side of the Y-axis based on a Cartesian coordinate system where the 0-0 point corresponds to the selected position may be compared. Specifically, the average of the grey values of the pixels within the inner ring may be compared first with the average of the grey values of the pixels of the middle ring to obtain a first binary value. Then the average of the grey values of the pixels of the inner ring may be compared to the average of the grey values of the pixels in the outer ring to obtain a second binary value. Then, the average of the grey values of the pixels within the inner ring may be compared with the average of the grey values of the pixels in the middle and the outer ring to obtain a third binary value. Furthermore, the average of the grey values of the pixels present in the inner and middle ring may be compared with the average of the grey values of the pixels present in the outer ring to obtain a fourth binary value. Furthermore, the average of the grey values of the pixels above the X-axis is compared to the average of the grey values of the pixels below the X-axis. Similarly, the average of the grey values of the pixels on the right hand side of the Y-axis is compared to the average of the grey values of the pixels on the left hand side of the Y-axis. Thus, in total six binary values are determined at each selected position. These six binary values for each individual position may have the following format "110011", "111001", "100011" and the like.

In a preferred embodiment of the invention, the positions on the iris are arranged in a form of a pattern. For an idealised situation the pupil of an eye is circular and located in the center of the iris. Furthermore, the iris/limbus border is circular and the center thereof is the same as the center of the pupil. Thus, for this idealised situation the length of a radial line starting from any point of the iris/pupil border to a corresponding point at the iris/limbus border is always the same. For such an idealised situation an example of a pattern may have a plurality of positions being arranged on a plurality of radial lines which are angularly spaced wherein on each radial line between the iris/pupil border and the iris/limbus border spaced positions are selected. Thus, those positions may be placed on a number of circular rings within the area of the iris. The angular distance between radial lines is preferably equal. The distance between circular rings is preferably equal such that the positions on the radial line are equidistant.

Such a reference pattern for an idealised situation of an eye will form the basis for any analysis of a real eye where the iris/pupil border may be non-circular and where the iris/limbus border may be non-circular and where the center of the iris/pupil border may deviate from the center of the iris/limbus border. For such a real eye the reference pattern will be scaled in a manner that the structure of the iris at a plurality of positions may be compared regardless of the size of the pupil in particular regardless whether the eye is dilated or undilated. Preferably, scaling of the pattern is performed based on the distance information between a certain point at the iris/pupil border and a corresponding point at the iris/limbus border.

In particular, for an undilated eye having a small pupil and a large area for the iris, such a region for investigation may have a ring structure. On the other hand, for a dilated eye, the pupil is bigger and the area of the iris is correspondingly smaller. The ring of the limbus is always the same. In this analysis it has to be taken into account that the center of the pupil may be different for the undilated eye and the dilated eye. Thus, the plurality of positions and the shape of the area of investigation around a certain position of the pattern is different for the dilated and the undilated eye, i. e. the circular rings may correspond to elliptical rings.

Preferably, the scaling has to be done individually for each selected position. According to this principle, the relationship of the length of a line connecting a point on the outer edge of the pupil and the corresponding point on the edge of the limbus for the dilated eye and the length for the undilated eye is taken as a scaling factor. According to an example, two arrows drawn from the center of the iris/pupil border and the center of the iris/limbus border are parallel and the point intersecting with the iris/pupil border and the iris/limbus border are connected by said line.

According to a preferred embodiment of the invention the structure at 980 positions is analysed for determining the uniformity of the structure of the iris. Further 980 positions are used for determining how great the changes are of the grey values. Both analysis are repeated for another change of frequency which is related to the difference of grey values. Thus in total 3,920 positions are analysed.

The image processing unit 14 provides image data by analysing said positions arranged in said pattern. The image data are provided to the generating unit 16. The generating unit 16 provides an iris code with reference to position data obtained for the eye under investigation. The digital iris code in the system described above will have 3,920 words, each having six binary bits, for example "110011", "111001", "100011" and the like. This digital iris code is unique for any eye of any person and may be used for identification of the person. The digital iris code may be arranged in the form of at least one matrix. This matrix may be related to the pattern used for choosing the plurality of positions of the iris.

In the system of FIG. 1 the diagnosis data of Zywave aberrometer 18 and the digital iris code are provided to an input/output device 20. In a preferred embodiment these data together with reference positional data are stored on a chip card for a patient. The data may be used in a later diagnosis or treatment of the respective eye of a patient.

FIG. 2 shows a schematic illustration of a preferred second embodiment of the invention which comprises a laser 32, a control means 34 and scanning means 36. It further comprises an image pick-up unit 12, an image processing unit 14, an image generating unit 16, and an input/output device 22. In addition, a second image pick-up unit is provided. Both image pick-up units 12 and 13 are arranged at an angle in a manner such that tracking in the direction of the Z-axis is possible as will be described below.

The embodiment shown in FIG. 2 is just an example whereas the invention may be used with any tye of ophthalmic unit for performing diagnosis and/or treatment of the eye.

At the beginning of any diagnosis or treatment of the eye a digital iris code is generated in the same way as described with reference to the embodiment shown in FIG. 1. The digital iris code is provided to a comparator being part of said control means 34 which compares the digital iris code with a previously acquired iris code stored in a storage means. In the example shown the previously acquired iris code is loaded from a chip card 24 by means of an input/output device 22. Based on a correlation process, the present iris code and the previously acquired iris code are compared. Based on the comparison result it is judged whether the eye under investigation is identical to the eye previously diagnosed. In case identity is confirmed, the system according to the invention will perform further diagnosis and/or treatment of the eye, otherwise a corresponding information will be outputted and/or any diagnosis and/or treatment will not be performed.

When comparing the present digital iris code with the previously acquired digital iris code both iris codes have to be compared for a number of relative rotational positions. In a preferred embodiment either the present iris code or the iris code obtained at the diagnosis site is recalculated by a modification unit such that a digital iris code is obtained for each one of possible rotational positions within a rotational range of preferably +/−14°. In total, there may be 84 rotational positions based on the calculation of range of 28° provided that three rotational positions are recalculated per degree. With other words, one single matrix representing the digital iris code obtained at the diagnosis site may be compared with each of 84 matrices calculated based on the present digital iris code. Effectively, the 84 different matrices for the corresponding 84 rotational positions of an image taken of an eye of one person could be regarded as 84 different eyes of persons which are compared to the matrix obtained at the diagnosis site. A determining unit determines the highest correlation between said present iris code and said previously acquired iris code being modified over a predetermined range of relative rotation.

According to the present invention the false match probability is achieved where at least 62% of all binary values correspond to each other in the previously acquired matrix at the present matrix, i. e. the matrix corresponding to the digital iris code at the treatment site and any of matrices previously stored in the system.

Rotational Alignment

The rotational alignment of diagnosis data and/or corresponding treatment data is performed based on the feature of the iris recognition unit. When comparing the present digital iris code obtained from the eye under investigation with a previously acquired iris code a correlation process is performed for a number of different rotational positions. The result showing the best match between the present digital iris code and the rotated digital iris code is taken for determining the rotational deviation of the eye at the treatment site with reference to the eye at the diagnosis site. This value for the rotational deviation is used for the rotational alignment of the ophthalmic unit. With other words, the diagnosis data and/or the respective treatment data are referenced to the present position of the eye.

At the treatment site the person is usually laying down on a bed below the treatment laser. In this situation the eye is rotationally displaced with respect to the position where the person is sitting. Therefore, any ablation pattern derived from the wavefront information of the Zywave aberrometer needs to be aligned corresponding to said rotational displacement. In addition, an X-Y-shift is usually present depending on the size of the pupil at the treatment site. Therefore, a translational correction and rotational correction of the position of the ablation pattern is performed. Thus, the data obtained from the chip card 24 comprises digital iris code, the X-Y-shift and the rotational position information of the eye. It further comprises the wavefront information of the Zywave aberrometer. At the laser system for performing refractive surgery a corresponding treatment pattern is calculated. This treatment pattern has to be applied to the cornea, i. e. the laser beam of an excimer laser 32 is guided under control of the control means 34 with a scanning means 36 to the correct positions of the eye. For adapting any movement of the eye of the patient during the treatment an X-Y-tracker 38 is used. This X-Y-tracker receives the images from a second camera 13. In a preferred embodiment the second camera 13 is faster than the first camera 12 whereas the first camera 12 has a higher resolution.

By means of X-Y-eye tracking the ablation pattern applied during refractive surgery follows any movement of the eye within a certain range. In case the eye moves out of this range, laser treatment will automatically be interrupted.

The presence of two image pick-up units 12 and 13 being arranged at an angle provides the additional feature of eye tracking in the direction of Z-axis, i. e. in the height direction. Both image pick-up units are arranged in such a way that the image taken from the first image pick-up unit 12 and the image taken from the second image pick-up unit 13 will only match at a certain height position of the eye to be treated. This feature allows to observe the height position of the eye along the Z-axis during the treatment. In addition a surgeon may use conventional means for adjusting a patient before starting the treatment. Such a conventional system may comprise two laser beams, i. e. a red laser beam and a green laser beam which are crossing at a certain point at the Z-axis of the system. This embodiment provides the advantage that by continuously checking the match of the two images taken by the first and the second image pick-up unit the treatment may automatically interrupt as soon as the patient is moving the head so that the eye is no longer at the correct height position.

The present invention can be seen in any individual feature described herein. Preferred embodiments of the invention are based on the combination of individual features or the combination of groups of individual features described herein. The scope of the present invention is not limited to the preferred embodiments described herein.

The invention claimed is:

1. System for acquiring data of an eye of a patient comprising a diagnosis unit for acquiring diagnosis data of the eye and
an iris recognition unit further comprising an image pick-up unit for acquiring an image of the eye and comparing means for acquiring an iris code of the eye by comparing grey values of at least two individual pixels at or in the neighbourhood of a plurality of positions.

2. The system of claim 1, further comprising processing means for determining coordinates of a pupil center of the eye.

3. System of claim 1 or 2, wherein the diagnosis data and/or the iris code and/or the center of the pupil of the eye are related to a common coordinate system.

4. System of claims 1 or 2, further comprising storage means for storing at least two of the following data, the diagnosis data, the iris code, the coordinates of the pupil center when the pupil is not dilated and the coordinates of the pupil center when the pupil is dilated, a data designating a patient and a respective eye and data regarding the acquisition of data.

5. System of claim 4, wherein the storage means comprises means for reading and writing data on a data carrier.

6. System of claims 1 or 2, wherein the diagnosis unit comprises an aberrometer which preferably acquires diagnosis data of the eye of a patient who is sitting up right.

7. System of claims 1 or 2 wherein the image pick-up unit is a video camera working in the infrared region.

8. System for aligning and for tracking of an eye of a patient with reference to an ophthalmic unit for performing a diagnosis and/or treatment of the eye comprising means for providing a previously acquired iris code of an eye of a patient, an iris recognition unit further comprising an image pick-up unit for acquiring an image of the eye and comparing means for acquiring an iris code by comparing grey values of at least two individual pixels at or in the neighbourhood of a plurality of positions of the eye under investigation as a present iris code, and
a comparator for comparing the present iris code with a previously acquired iris code and providing a comparison result, wherein said ophthalmic unit performs said diagnosis and/or treatment of the eye when said comparison result is greater than an identification determining level.

9. System of claim 8, wherein said comparator comprises means for performing correlation between said present iris code and said previously acquired iris code, wherein said present iris code is related to a first rotational position and said previously acquired iris code is related to a second rotational position,
a modification unit for modifying the present iris code and/or the previously acquired iris code such the relative position between the first rotational position and the second rotational position is changed, and a determining unit for determining the highest correlation between said present iris code and said previously acquired iris code being modified over a predetermined range of relative rotation.

10. System of claim 9, wherein the eye under investigation is aligned to the ophthalmic unit by said rotational shift corresponding to the highest correlation between the present iris code and the previously acquired iris code.

11. System of any of claims 8 to 10, further comprising processing means for determining coordinates of a pupil center of the eye under investigation, wherein the present coordinates of the pupil center are used in aligning and tracking the eye with reference to the ophthalmic unit.

12. System of any of claims 8 to 10, wherein the ophthalmic unit comprises a refractive surgery apparatus comprising an excimer laser for correction of refractive defects of the eye.

13. System of claim 12, wherein said refractive surgery system performs the correction of refracting defects based on diagnosis data previously acquired for said eye.

14. System of claim 12, comprising a first image pick-up unit having a high resolution for providing an image of the eye to the iris recognition unit and preferably a second image pick-up unit being preferably faster than said first image pick-up unit for providing images being used for tracking the eye with reference to the ophthalmic unit.

15. System of claim 14, wherein said first and said second image pick-up unit being arranged at an angle to each other such that the respective images taken of the eye matches at a predetermined height position of the eye under investigation.

16. System of claim 15, further comprising control means for performing the diagnosis and/or treatment of the eye by said ophthalmic unit when a match between said images of the first and said second image pick-up units is detected.

17. Iris recognition unit for use in a system for aligning and for tracking of an eye of a patient with reference to an ophthalmic unit for performing a diagnosis and/or treatment of the eye, said unit comprising
   an image pick-up unit for acquiring an image of the eye,
   an image processing unit for determining iris information at a plurality of positions of the image of the eye and
   a generating unit further comprising comparing means for generating an iris code based on said iris information at said plurality of positions of the image of the eye by comparing grey values of at least two individual pixels at or in the neighbourhood of said plurality of positions.

18. Iris recognition unit of claim 17 comprising means for determining the iris/pupil border and/or the iris/limbus border, wherein said image processing unit determines the plurality of positions based on the relative position of the iris/pupil border with respect to the iris/limbus border.

19. Iris recognition unit of claim 18, wherein said relative position of said iris/pupil border with respect to said iris/limbus border is calculated based on a deviation of a center point of the iris/pupil border with respect to a center point of the iris/limbus border, and/or the length of a radial line starting from a certain point at the iris/pupil border and ending at a corresponding point at the iris/limbus border.

20. Iris recognition unit of claim 18, wherein said comparing means compares the grey values of pixels present in at least one of the following regions, an inner ring surrounding a particular position, a middle ring, surrounding said inner ring, an outer ring surrounding said middle ring, the region above and below a horizontal axis and the region on the left side and the right hand side of a vertical axis going through said particular position.

21. Iris recognition unit of claim 17, wherein said image processing unit comprises comparing means for comparing grey values of at least two individual pixels at or in the neighbourhood at each respective position of said plurality of positions.

22. Iris recognition unit of claim 20, wherein said comparing means compares an average of the grey values of pixels within one of said regions with the average of grey values of pixels within a neighbouring region and provides the binary result for each comparison based on whether the difference of the respective average values is greater or smaller than a threshold value.

23. Iris recognition unit of any of claims 21 to 22, wherein said generating unit receives the comparison results as a set of binary values, preferably six binary values for each particular position and provides said iris code by arranging said sets of binary values in a predetermined order corresponding to the relative positions used in the image processing unit.

24. Iris recognition unit of claim 23, wherein the iris code comprises said sets of binary values in the form of at least one matrix.

25. Method for acquiring data of an eye of a patient comprising:
   acquiring diagnosis data of the eye, acquiring an image of the eye and acquiring an iris code by comparing grey values of at least two individual pixels at or in the neighbourhood of a plurality of positions.

26. The method of claim 25 further comprising determining coordinates of a pupil center of the eye and relating the diagnosis data, the iris code and the center of the pupil to a common coordinate system.

27. The method of claim 25 further comprising storing at least two of the following data, the diagnosis data, the iris code, the coordinates of the pupil center when the pupil is not dilated and the coordinates of the pupil center when the pupil is dilated, a data designating a patient and a respective eye and data regarding the acquisition of data.

28. Method for aligning and/or tracking of an eye of a patient with reference to an ophthalmic unit for performing a diagnosis and/or treatment of the eye comprising:
   providing a previously acquired iris code of an eye of the patient,
   acquiring an image of the eye and acquiring an iris code by comparing grey values of at least two individual pixels at or in the neighbourhood of a plurality of positions of the eye under investigation as a present iris code,
   comparing the present iris code with the previously acquired iris code and providing a comparison result, and
   performing said diagnosis and/or treatment of the eye when said comparison result is greater than an identification determining level.

29. The method of claim 28 wherein comparison of the present iris code with the previously acquired iris code comprises relating the present iris code to a first rotational position and relating the previous iris code to a second rotational position, modifying the present iris code and/or the previously acquired iris code such that that the relative position between the first rotational position and the second rotational position is changed, and determining the highest correlation between said present iris code and said previously acquired iris code as modified over a predetermined range of relative rotation.

30. The method of claim 29 further comprising aligning the eye to the ophthalmic unit by a rotational shift corresponding to the highest correlation between the present iris code and the previously acquired iris code.

31. Method for iris recognition comprising:
   acquiring an image of the eye,
   determining iris information at a plurality of positions of the image of the eye, and
   generating an iris code based on said iris information at said plurality of positions of the image of the eye by comparing grey values of at least two individual pixels at or in the neighbourhood of said plurality of positions.

32. The method of claim 27 further comprising determining the iris/pupil border and the iris/limbus border, wherein the plurality of positions are determined based on the relative position of the iris/pupil border with respect to the iris/limbus border.

33. The method of claim 32 wherein relative position of said iris/pupil border with respect to said iris/limbus border is calculated based on a deviation of a center point of the iris/pupil border with respect to a center point of the iris/limbus border, and/or the length of a radial line starting from a certain point at the iris/pupil border and ending at a corresponding point at the iris/limbus border.

34. The method of claim 33 wherein the grey values of pixels compared are selected from at least one of the following regions: an inner ring surrounding a particular position, a middle ring, surrounding said inner ring, an outer ring surrounding said middle ring, the region above and below a horizontal axis and the region on the left side and the right hand side of a vertical axis going through said particular position.

35. The method of claim 34 wherein an average of the grey values of pixels within one of said regions is compared with the average of grey values of pixels within a neighbouring region providing a binary result for each comparison based on whether the difference of the respective average values is greater or smaller than a threshold value.

36. The method of claim 35 comprising receiving the comparison results as a set of binary values and generating said iris code by arranging said sets of binary values in a predetermined order corresponding to the relative positions used in the image processing unit.

37. The method of claim 36 wherein six binary values are received for each particular position.

* * * * *